US006834204B2

(12) United States Patent
Ostroff et al.

(10) Patent No.: US 6,834,204 B2
(45) Date of Patent: Dec. 21, 2004

(54) METHOD AND APPARATUS FOR INDUCING DEFIBRILLATION IN A PATIENT USING A T-SHOCK WAVEFORM

(75) Inventors: Alan H. Ostroff, San Clemente, CA (US); William J. Rissmann, Coto de Caza, CA (US); Gust H. Bardy, Seattle, WA (US)

(73) Assignee: Cameron Health, Inc., San Clemente, CA (US)

( * ) Notice: Subject to any disclaimer, the term of this patent is extended or adjusted under 35 U.S.C. 154(b) by 233 days.

(21) Appl. No.: 10/011,527

(22) Filed: Nov. 5, 2001

(65) Prior Publication Data

US 2003/0088286 A1 May 8, 2003

(51) Int. Cl.$^7$ ................................................ A61N 1/00
(52) U.S. Cl. ............................................................. 607/2
(58) Field of Search ............. 607/2, 5, 7; 600/515–518, 600/521, 510

(56) References Cited

U.S. PATENT DOCUMENTS

| | | |
|---|---|---|
| 3,653,387 A | 4/1972 | Ceier |
| 3,710,374 A | 1/1973 | Kelly |
| 3,911,925 A | 10/1975 | Tillery, Jr. |
| 4,157,720 A | 6/1979 | Greatbatch |
| 4,191,942 A | 3/1980 | Long |
| 4,223,678 A | 9/1980 | Langer et al. |
| 4,248,237 A | 2/1981 | Kenny |
| 4,291,707 A | 9/1981 | Heilman et al. |
| 4,314,095 A | 2/1982 | Moore et al. |
| 4,402,322 A | 9/1983 | Duggan |
| 4,407,288 A | 10/1983 | Langer et al. |
| 4,424,818 A | 1/1984 | Doring et al. |
| 4,602,637 A | 7/1986 | Elmqvist et al. |
| 4,765,341 A | 8/1988 | Mower et al. |
| 4,800,883 A | 1/1989 | Winstrom |
| 4,830,005 A | 5/1989 | Woskow |
| 5,109,842 A | 5/1992 | Adinolfi |
| 5,129,392 A * | 7/1992 | Bardy et al. .................... 607/2 |
| 5,133,353 A | 7/1992 | Hauser |
| 5,144,946 A | 9/1992 | Weinberg et al. |
| 5,184,616 A | 2/1993 | Weiss |
| 5,191,901 A | 3/1993 | Dahl et al. |

(List continued on next page.)

FOREIGN PATENT DOCUMENTS

| | | |
|---|---|---|
| DE | 298 01 807 U1 | 7/1998 |
| EP | 0 095 727 A1 | 12/1983 |
| EP | 0 316 616 A2 A3 | 5/1989 |
| EP | 0 347 353 A1 | 12/1989 |

(List continued on next page.)

OTHER PUBLICATIONS

Friedman, Richard A. et al., "Implantable Defibrillators In Children: From Whence to Shock," *Journal of Cardiovascular Electrophysiology*, vol. 12, No. 3, Mar. 2001, pp. 361–362.

Gradaus, Rainer et al., "Nonthoracotomy Implantable Cardioverter Defibrillator Placement in Children: Use of Subcutaneous Array Leads and Abdominally Placed Implantable Cardioverter Defibrillators in Children," *Journal of Cardiovascular Electrophysiology*, vol. 12, No. 3, Mar. 2001, pp. 356–360.

(List continued on next page.)

*Primary Examiner*—Jeffrey R. Jastrzab
(74) *Attorney, Agent, or Firm*—Crompton, Seager & Tufte, LLC (57) ABSTRACT

A shock is delivered on the T-wave of a patient's cardiac waveform by first detecting the occurrence of a QRS complex in the waveform and using that detection to set up for detection of the following T-wave. Narrowband filtering is used to first select the QRS complex and thereafter the T-wave, while peak detection is employed to define the actual occurrence of the respective waveforms. The capability is also provided to deliver the shock at a manually selected interval after QRS detection or after a coupling interval in a pacing application.

36 Claims, 3 Drawing Sheets

U.S. PATENT DOCUMENTS

| | | |
|---|---|---|
| 5,203,348 A | 4/1993 | Dahl et al. |
| 5,230,337 A | 7/1993 | Dahl et al. |
| 5,255,692 A | 10/1993 | Neubauer et al. |
| 5,261,400 A | 11/1993 | Bardy |
| 5,300,106 A | 4/1994 | Dahl et al. |
| 5,331,966 A | 7/1994 | Bennett et al. |
| 5,342,407 A | 8/1994 | Dahl et al. |
| 5,366,496 A | 11/1994 | Dahl et al. |
| 5,376,103 A | 12/1994 | Anderson et al. |
| 5,376,104 A | 12/1994 | Sakai et al. |
| 5,385,574 A | 1/1995 | Hauser et al. |
| 5,391,200 A | 2/1995 | KenKnight et al. |
| 5,411,539 A | 5/1995 | Neisz |
| 5,411,547 A | 5/1995 | Causey, III |
| 5,413,591 A | 5/1995 | Knoll |
| 5,509,923 A | 4/1996 | Middleman et al. |
| 5,509,928 A | 4/1996 | Acken |
| 5,531,765 A | 7/1996 | Pless |
| 5,531,766 A | 7/1996 | Kroll et al. |
| 5,534,019 A | 7/1996 | Paspa |
| 5,601,607 A | 2/1997 | Adams |
| 5,603,732 A | 2/1997 | Dahl et al. |
| 5,643,328 A | 7/1997 | Cooke et al. |
| 5,645,586 A | 7/1997 | Meltzer |
| 5,658,317 A | 8/1997 | Haefner et al. |
| 5,674,260 A | 10/1997 | Weinberg |
| 5,690,648 A | 11/1997 | Fogarty et al. |
| 5,690,683 A | 11/1997 | Haefner et al. |
| 5,697,953 A | 12/1997 | Kroll et al. |
| 5,713,926 A | 2/1998 | Hauser et al. |
| 5,718,242 A * | 2/1998 | McClure et al. ............ 600/515 |
| 5,766,226 A | 6/1998 | Pedersen |
| 5,776,169 A | 7/1998 | Schroeppel |
| 5,814,090 A | 9/1998 | Latterell et al. |
| 5,836,976 A | 11/1998 | Min et al. |
| 5,895,414 A | 4/1999 | Sanchez-Zambrano |
| 5,919,211 A | 7/1999 | Adams |
| 5,919,222 A | 7/1999 | Hjelle et al. |
| 5,925,069 A | 7/1999 | Graves et al. |
| 5,935,154 A | 8/1999 | Westlund |
| 5,941,904 A | 8/1999 | Johnston et al. |
| 6,014,586 A | 1/2000 | Weinberg et al. |
| 6,026,325 A | 2/2000 | Weinberg et al. |
| 6,058,328 A | 5/2000 | Levine et al. |
| 6,093,173 A | 7/2000 | Balceta et al. |
| H1905 H | 10/2000 | Hill |
| 6,128,531 A | 10/2000 | Campbell-Smith |
| 6,144,866 A | 11/2000 | Miesel et al. |
| 6,185,450 B1 | 2/2001 | Seguine et al. |
| 6,411,844 B1 | 6/2002 | Kroll et al. |
| 2001/0027330 A1 | 10/2001 | Sullivan et al. |

FOREIGN PATENT DOCUMENTS

| | | |
|---|---|---|
| EP | 0 517 494 B1 | 12/1992 |
| EP | 0 517 494 A3 | 12/1992 |
| EP | 0 518 599 B1 | 12/1992 |
| EP | 0 518 599 A2 | 12/1992 |
| EP | 0 536 873 B1 | 4/1993 |
| EP | 0 586 858 B1 | 3/1994 |
| EP | 0 627 237 A1 | 12/1994 |
| EP | 0 641 573 A3 | 3/1995 |
| EP | 0 641 573 A2 | 3/1995 |
| EP | 0 677 301 A1 | 10/1995 |
| EP | 0 917 887 A1 | 5/1999 |
| EP | 0 923 130 A1 | 6/1999 |
| EP | 1 000 634 A1 | 5/2000 |
| WO | WO 93/19809 A1 | 10/1993 |
| WO | WO 97/29802 A2 | 8/1997 |
| WO | WO 98/25349 A1 | 6/1998 |
| WO | WO 99/03534 A1 | 1/1999 |
| WO | WO 99/37362 A1 | 7/1999 |
| WO | WO 99/53991 A1 | 10/1999 |
| WO | WO 00/41766 A1 | 7/2000 |
| WO | WO 00/50120 A1 | 8/2000 |
| WO | WO 01/43649 A1 | 6/2001 |
| WO | WO 01/56166 A2 | 8/2001 |
| WO | WO 02/22208 A3 | 3/2002 |
| WO | WO 02/22208 A2 | 3/2002 |
| WO | WO 02/24275 A3 | 3/2002 |
| WO | WO 02/24275 A2 | 3/2002 |
| WO | WO 02/068046 A1 | 9/2002 |
| WO | WO 03/018121 A2 | 3/2003 |

OTHER PUBLICATIONS

Mirowski, M. et al., "Automatic Detection and Defibrillation of Lethal Arrhythmias– A New Concept," *JAMA*, vol. 213, No. 4, Jul. 27, 1970, pp. 615–616.

Olson, Walter H. et al., "Onset and Stability for Ventricular Tachyarrhythmia Detection in an Implantable Pacer–Cardioverter–Defribrillator," *IEEE*, (1987) pp. 167–170.

Schuder, John C., "Completely Implanted Defibrillator," *JAMA*, vol. 214, No. 6, Nov. 9, 1970. p. 1123 (single sheet).

Schuder, John C., "The Role of an Engineering Oriented Medical Research Group in Developing Improved Methods and Devices for Achieving Ventricular Defibrillation: The University of Missouri Experience," *PACE*, vol. 16, Jan. 1993, pp. 95–124.

Schuder, John C. et al., "Experimental Ventricular Defibrillation with an Automatic and Completely Implanted System," *Trans. Amer. Soc. Artif. Int. Organs*, vol. XVI (1970) pp. 207–212.

Schuder, John C. et al., "Standby Implanted Defibrillators," *Arch Intern. Med*, vol. 127, Feb. 1971, p. 317 (single sheet).

Schuder, John C. et al., "Transthoracic Ventricular Defibrillation in the Dog with Truncated and Untruncated Exponential Stimuli," *IEEE Transactions on Bio–Medical Engineering*, vol. BME–18, No. 6, Nov. 1971, pp. 410–415.

Tietze U. et al., "Halbleiter–Schaltungstechnik," ©Springer–Verlag (Berlin, Germany), (1991), pp. 784–786.

Walters, R.A. et al., "Analog to Digital Conversion Techniques in Implantable Devices," *Annual International Conference of the IEEE Engineering in Medicine and Biology Society*, vol. 13 No. 4(1991) p. 1674–1676.

* cited by examiner

METHOD AND APPARATUS FOR INDUCING DEFIBRILLATION IN A PATIENT USING A T-SHOCK WAVEFORM

CROSS-REFERENCE TO RELATED APPLICATIONS

The invention of the present application may find application in systems such as are disclosed in U.S. patent application entitled "SUBCUTANEOUS ONLY IMPLANTABLE CARDIOVERTER-DEFIBRILLATOR AND OPTIONAL PACER," having Ser. No. 09/663,607, filed Sep. 18, 2000, pending, and U.S. patent application entitled "UNITARY SUBCUTANEOUS ONLY IMPLANTABLE CARDIOVERTER-DEFIBRILLATOR AND OPTIONAL PACER," having Ser. No. 09/663,606, filed Sep. 18, 2000, pending, of which both applications are assigned to the assignee of the present application, and the disclosures of both applications are hereby incorporated by reference.

In addition, the foregoing applications are related to the U.S. patent application entitled "DUCKBILL-SHAPED IMPLANTABLE CARDIOVERTER-DEFIBRILLATOR AND METHOD OF USE," U.S. patent application entitled "CERAMICS AND/OR OTHER MATERIAL INSULATED SHELL FOR ACTIVE AND NON-ACTIVE S-ICD CAN," U.S. patent application entitled "SUBCUTANEOUS ELECTRODE FOR TRANSTHORACIC CONDUCTION WITH IMPROVED INSTALLATION CHARACTERISTICS," U.S. patent application entitled "SUBCUTANEOUS ELECTRODE WITH IMPROVED CONTACT SHAPE FOR TRANSTHORACIC CONDUCTION," U.S. patent application entitled "SUBCUTANEOUS ELECTRODE FOR TRANSTHORACIC CONDUCTION WITH HIGHLY MANEUVERABLE INSERTION TOOL," U.S. patent application entitled "SUBCUTANEOUS ELECTRODE FOR TRANSTHORACIC CONDUCTION WITH LOW-PROFILE INSTALLATION APPENDAGE AND METHOD OF DOING SAME," U.S. patent application entitled "SUBCUTANEOUS ELECTRODE FOR TRANSTHORACIC CONDUCTION WITH INSERTION TOOL," U.S. patent application entitled "METHOD OF INSERTION AND IMPLANTATION FOR IMPLANTABLE CARDIOVERTER-DEFIBRILLATOR CANISTERS," U.S. patent application entitled "CANISTER DESIGNS FOR IMPLANTABLE CARDIOVERTER-DEFIBRILLATORS," U.S. patent application entitled "RADIAN CURVED IMPLANTABLE CARDIOVERTER-DEFIBRILLATOR CANISTER," U.S. patent application entitled "CARDIOVERTER-DEFIBRILLATOR HAVING A FOCUSED SHOCKING AREA AND ORIENTATION THEREOF," U.S. patent application entitled "BIPHASIC WAVEFORM FOR ANTI-BRADYCARDIA PACING FOR A SUBCUTANEOUS IMPLANTABLE CARDIOVERTER-DEFIBRILLATOR," and U.S. patent application entitled "BIPHASIC WAVEFORM FOR ANTI-TACHYCARDIA PACING FOR A SUBCUTANEOUS IMPLANTABLE CARDIOVERTER-DEFIBRILLATOR," the disclosures of which applications are hereby incorporated by reference.

FIELD OF THE INVENTION

The present invention relates to apparatus and methods useful in connection with performing electrical cardioversion/defibrillation and optional pacing of the heart.

BACKGROUND OF THE INVENTION

Defibrillation/cardioversion is a technique employed to counter arrhythmic heart conditions including some tachycardias in the atria and/or ventricles. Typically, electrodes are employed to stimulate the heart with electrical impulses or shocks, of a magnitude substantially greater than pulses used in cardiac pacing.

Defibrillation/cardioversion systems include body implantable electrodes that are connected to a hermetically sealed container housing the electronics, battery supply and capacitors. The entire system is referred to as implantable cardioverter/defibrillators (ICDs). The electrodes used in ICDs can be in the form of patches applied directly to epicardial tissue, or, more commonly, are on the distal regions of small cylindrical insulated catheters that typically enter the subclavian venous system, pass through the superior vena cava and, into one or more endocardial areas of the heart. Such electrode systems are called intravascular or transvenous electrodes. U.S. Pat. Nos. 4,603,705, 4,693,253, 4,944,300, 5,105,810, the disclosures of which are all incorporated herein by reference, disclose intravascular or transvenous electrodes, employed either alone, in combination with other intravascular or transvenous electrodes, or in combination with an epicardial patch or subcutaneous electrodes. Compliant epicardial defibrillator electrodes are disclosed in U.S. Pat. Nos. 4,567,900 and 5,618,287, the disclosures of which are incorporated herein by reference. A sensing epicardial electrode configuration is disclosed in U.S. Pat No. 5,476,503, the disclosure of which is incorporated herein by reference.

In addition to epicardial and transvenous electrodes, subcutaneous electrode systems have also been developed. For example, U.S. Pat. Nos. 5,342,407 and 5,603,732, the disclosures of which are incorporated herein by reference, teach the use of a pulse monitor/generator surgically implanted into the abdomen and subcutaneous electrodes implanted in the thorax. This system is far more complicated to use than current ICD systems using transvenous lead systems together with an active can electrode and therefore it has no practical use. It has in fact never been used because of the surgical difficulty of applying such a device (3 incisions), the impractical abdominal location of the generator and the electrically poor sensing and defibrillation aspects of such a system.

Recent efforts to improve the efficiency of ICDs have led manufacturers to produce ICDs which are small enough to be implanted in the pectoral region. In addition, advances in circuit design have enabled the housing of the ICD to form a subcutaneous electrode. Some examples of ICDs in which the housing of the ICD serves as an optional additional electrode are described in U.S. Pat. Nos. 5,133,353, 5,261,400, 5,620,477, and 5,658,321 the disclosures of which are incorporated herein by reference.

ICDs are now an established therapy for the management of life threatening cardiac rhythm disorders, primarily ventricular fibrillation (V-Fib). ICDs are very effective at treating V-Fib, but are therapies that still require significant surgery.

As ICD therapy becomes more prophylactic in nature and used in progressively less ill individuals, especially children at risk of cardiac arrest, the requirement of ICD therapy to use intravenous catheters and transvenous leads is an impediment to very long term management as most individuals will begin to develop complications related to lead system malfunction sometime in the 5–10 year time frame, often earlier. In addition, chronic transvenous lead systems, their reimplantation and removals, can damage major cardiovascular venous systems and the tricuspid valve, as well as result in life threatening perforations of the great vessels and heart. Consequently, use of transvenous lead systems, despite their many advantages, are not without their chronic patient management limitations in those with life expectancies of >5 years. The problem of lead complications is even greater in children where body growth can substantially alter transvenous lead function and lead to additional cardiovascular problems and revisions. Moreover, transvenous ICD systems also increase cost and require specialized interventional rooms and equipment as well as special skill for insertion. These systems are typically implanted by cardiac electrophysiologists who have had a great deal of extra training.

In addition to the background related to ICD therapy, the present invention requires a brief understanding of a related therapy, the automatic external defibrillator (AED). AEDs employ the use of cutaneous patch electrodes, rather than implantable lead systems, to effect defibrillation under the direction of a bystander user who treats the patient suffering from V-Fib with a portable device containing the necessary electronics and power supply that allows defibrillation. AEDs can be nearly as effective as an ICD for defibrillation if applied to the victim of ventricular fibrillation promptly, i.e., within 2 to 3 minutes of the onset of the ventricular fibrillation.

AED therapy has great appeal as a tool for diminishing the risk of death in public venues such as in air flight. However, an AED must be used by another individual, not the person suffering from the potential fatal rhythm. It is more of a public health tool than a patient-specific tool like an ICD. Because >75% of cardiac arrests occur in the home, and over half occur in the bedroom, patients at risk of cardiac arrest are often alone or asleep and can not be helped in time with an AED. Moreover, its success depends to a reasonable degree on an acceptable level of skill and calm by the bystander user.

What is needed therefore, especially for children and for prophylactic long term use for those at risk of cardiac arrest, is a combination of the two forms of therapy which would provide prompt and near-certain defibrillation, like an ICD, but without the long-term adverse sequelae of a transvenous lead system while simultaneously using most of the simpler and lower cost technology of an AED. What is also needed is a cardioverter/defibrillator that is of simple design and can be comfortably implanted in a patient for many years.

One feature desirable in such a cardioverter/defibrillator is one which permits a physician in the field to test the energy level of an implanted ICD to ensure that the ICD will deliver an effective defibrillating pulse. Once the physician has determined that a sufficient amount of energy will be delivered to achieve defibrillation, he or she can complete the implant procedure.

Figure 1:
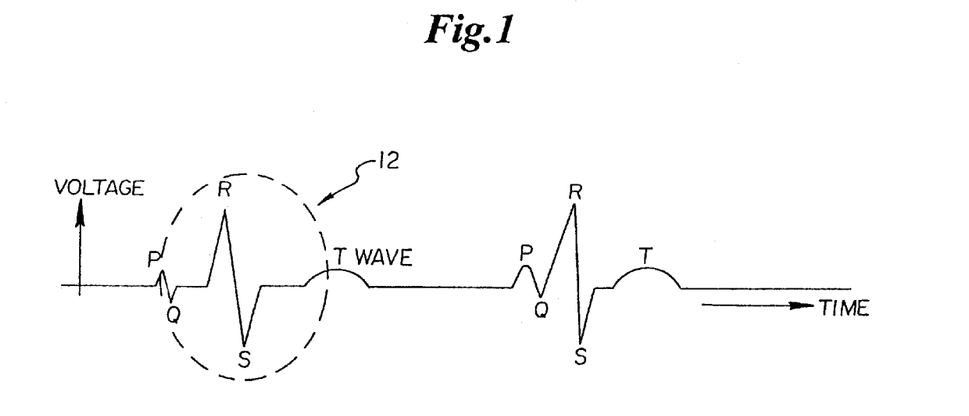
FIG. 1 is a waveform diagram useful in illustrating various embodiments of the invention.

In order to test the energy level of the ICD, it is necessary to induce fibrillation and then observe whether the ICD counteracts it. To induce fibrillation, a shock is delivered to a patient which coincides with ventricular repolarization. This repolarization coincides with the T-wave portion of the patient's cardiac waveform shown in FIG. 1. This waveform includes the P, Q, R, and S peaks, followed by the T-wave. The Q, R, and S pulses may collectively be referred to as the "QRS Complex" 12, or the "R-wave." Thus, delivering a small energy shock in coincidence with occurrence of the T-wave will induce fibrillation.

In pacing systems, delivering a shock on the T-wave is relatively straight-forward because, in such systems, pacing is done at a rate which exceeds the patient's intrinsic heart rhythm, and the ventricle is stimulated with a programmed constant coupling interval. In contrast, when the patient's heart is free-running, the distance between the T-wave and the QRS complex can vary.

Figure 2:
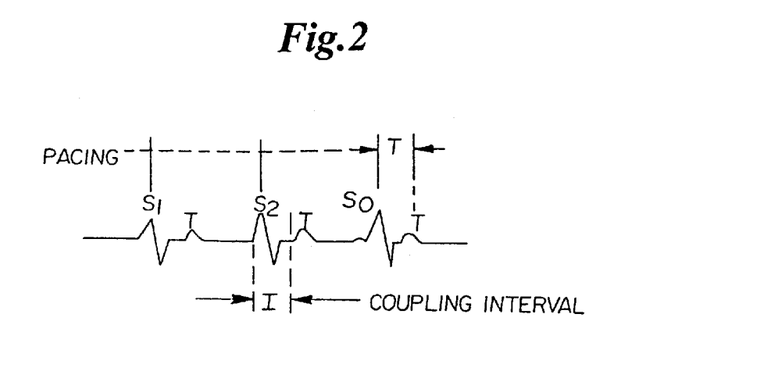
FIG. 2 is a waveform diagram illustrating pacing of the heart.

Thus, with pacing control, one knows precisely when the QRS complex and the T-wave will occur. As shown in FIG. 2, a first pacing QRS signal $S_1$ is applied and, after an initial response or "coupling" interval I, a T-wave occurs. Then, after the coupling interval, another pacing QRS signal $S_2$ is applied and, after a second coupling interval I, another T-wave occurs. It is then possible to determine exactly when the T-wave will occur from examining the response intervals. Accordingly, with pacing, one simply defines how many pulses $S_1$, $S_2$, etc., to deliver and then delivers a shock at the desired position on the T-wave. Typically, the shock is anywhere from a half (0.5) a joule to 350 joules and may be delivered as a monophasic or biphasic pulse or other signal shape.

SUMMARY OF THE INVENTION

In pacing systems, one has the luxury of entraining the heart because an electrical lead is positioned in the heart. The present invention, however, is intended to be useful in systems where a lead is not located in the heart and where pacing is not available. Accordingly, the subject invention facilitates employing the patient's own intrinsic cardiac signal to control delivery of a shock on the T-wave.

Since the patient's intrinsic heart rate varies, the timing of the T-wave varies. Accordingly, according to the invention, the occurrence of the T-wave may be automatically detected and a shock delivered in response to the detection. The invention further contemplates manual and pacing embodiments where the timing of the shock is manually set to occur at a selected point in time following automatic detection of the QRS complex or R-wave.

BRIEF DESCRIPTION OF THE DRAWINGS

For a better understanding of the invention, reference is now made to the drawings where like numerals represent similar objects throughout the figures and wherein.

DETAILED DESCRIPTION OF ILLUSTRATIVE EMBODIMENTS

Figure 3:
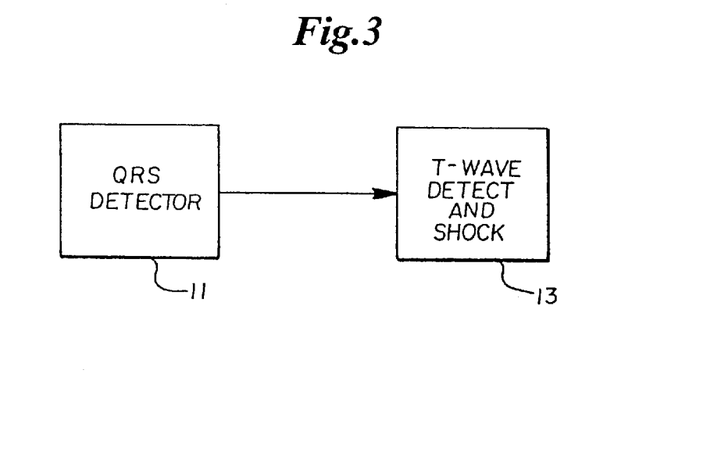
FIG. 3 is a block diagram illustrative of the method and apparatus employed in the preferred embodiment.

An illustrative embodiment of the invention utilizes the approach shown in FIG. 3. This approach involves a first detection 11 of the QRS complex portion of the waveform (also referred to at times as the "R-wave"). In response to detection of the R-wave, the system is set up to expect and perform detection of the T-wave, as represented by block 13 of FIG. 1.

Figure 4:
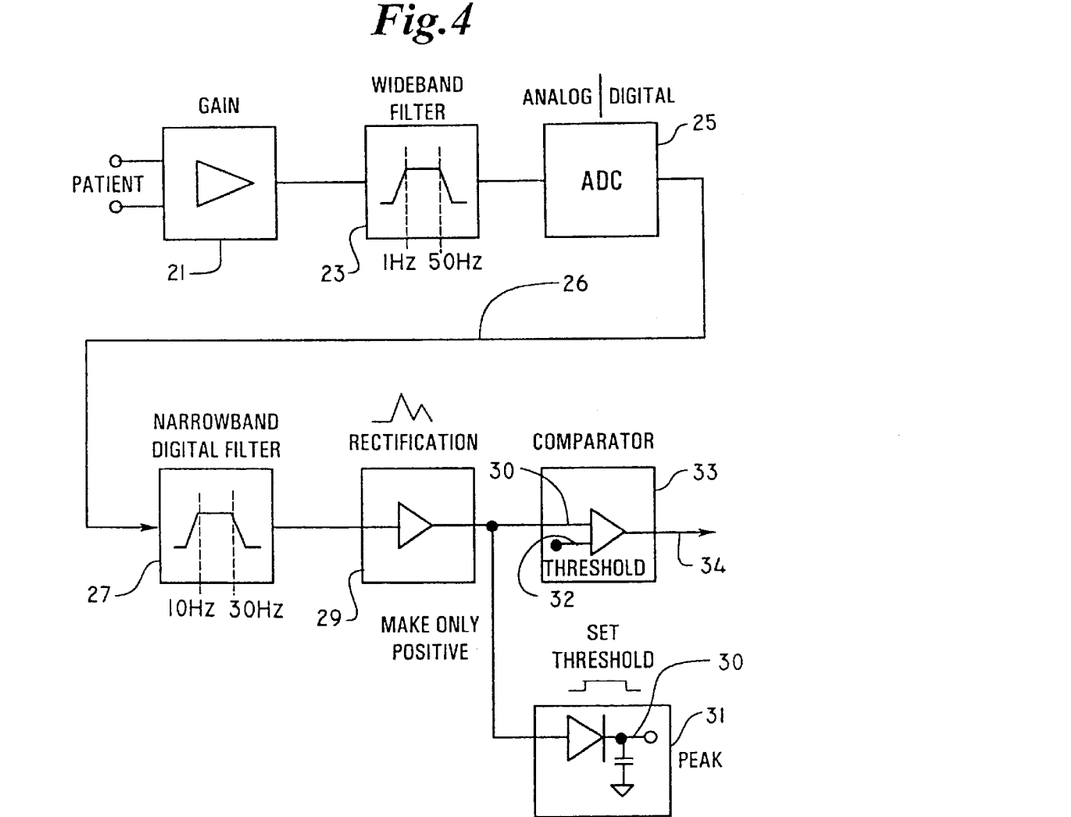
FIG. 4 is a schematic circuit diagram illustrating an embodiment of a QRS detector.

A circuit and method for detecting the QRS complex is illustrated in FIG. 4. This circuit employs an electrode which connects a patient to the input of a gain stage 21, which may comprise an amplifier. The output signal of the gain stage 21 is supplied to an input of a wide band filter 23, whose output is provided to an analog to digital (A/D) converter 25. The digital output generated by the A/D converter 25 is supplied to a narrow band filter 27. The filtered signal generated by the narrow band filter 27 is then rectified by a rectification stage 29, whose output is then supplied to a peak detector 31. The output of the peak detector 31 forms a first input 30 to a comparator 33 whose second input 32 is a selectable threshold voltage input. The wideband filter 23 may have a 3 dB bandwidth of, e.g., 1 hertz to 50 hertz, while the 3 dB bandwidth of the narrow band filter 27 may be, e.g., 10 hertz to 30 hertz.

As may be appreciated, the functions implemented in FIG. 4 after digital conversion by the A/D converter 25 may be, and preferably are implemented by software programming, e.g., of a microprocessor or nanoprocessor, to perform filtering, rectification, and peak detection. Such software can be programmed to examine a few intrinsic heartbeats to establish an average peak height of the peak R-wave and an average height of the peak T-wave and use these averages to set the capacitor thresholds accordingly.

The filtering employed in FIG. 3 accentuates the R-wave and attenuates the effect of the T-wave because the T-wave is a low frequency, far field signal.

Thus, in operation of the QRS detector 11, the wide band signal passes through a narrow band filter 27 such that signal components other than those corresponding to the R-wave, the high frequency content signal, are eliminated. The T-wave is particularly eliminated by moving the passband of the filter 27 up to 10 Hz, from 1 Hz, thus eliminating the low frequency content of the signal. Rectification by the rectifier 29 results in a signal which has only a positive value. When the peak detected rectified signal on output 31 exceeds the threshold level on input 32, detection of QRS is signaled by a signal on the output 34 of the comparator 33.

Another way of detecting the QRS complex or R-wave is to employ a gain stage, a wide band filter, and A/D whose output is filtered two ways to detect the R-wave (QRS complex). Such an approach may be implemented by a circuit which employs first and second comparators to respectively detect the positive-going "R" waves or negative-going R-waves. A narrow band filter centered around where the R-wave is, e.g., at 20 Hz, precedes the comparators. As will be appreciated, the two comparator approach is an alternative which avoids rectification and hence the rectification stage 29 of FIG. 4.

In looking for a QRS peak, one may employ various techniques to improve detection, e.g., to avoid detecting a localized peak instead of the real peak. Thus, an integration may be implemented to ensure that the detected transition is a decline from the real peak value.

Another approach illustrated in FIG. 4 is to simply set a threshold so that when the QRS signal exceeds that threshold an output is produced by the comparator such that the system knows that an R-wave has occurred.

With respect to selecting the threshold, one may employ the approach used in some pacemakers of setting a fixed threshold, e.g., of 0.8 milivolts, 2 milivolts, or 3 milivolts. Another approach is to employ an automatic gain control system. One way to implement automatic gain control is to employ the system software to average the value of a number of successive peaks and set the threshold to a percentage of the average peak value.

Thus, the characteristics of the QRS detection 11 are such that it reliably detects a particular "fiducial point" of the QRS complex and rejects T-waves. The term "fiducial point of the QRS complex" is employed because various points can be detected in various implementations. For example, one may detect a signal peak as discussed above, the onset of the QRS signal, or a zero crossing, e.g., a point where the QRS signal goes across the "ISO" baseline. Thus, one may look at the circuitry after filtering in FIG. 4 as the QRS detector, or the "R-wave" detector.

Figure 5:
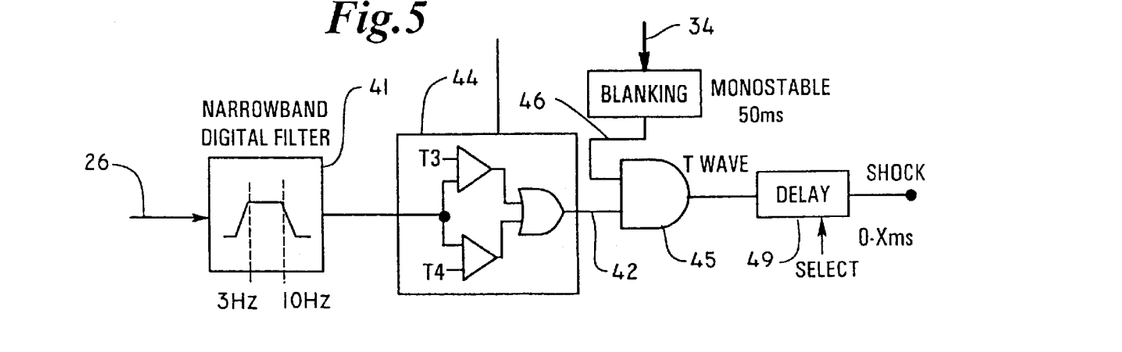
FIG. 5 is a schematic circuit diagram of an illustrative embodiment of T-wave detection and shock delivery circuitry.

A system for detecting the T-wave is illustrated in FIG. 5. The system differs from that of FIG. 4 by taking off in after the ADC 24 (FIG. 4) as noted by line 26. Instead of going to a QRS narrowband filter 27 (FIG. 4), the T-wave detection system goes to a T-wave filter 41 as shown in FIG. 5. The T-wave filter 41 is a narrow band filter centered around the frequency content of the T-wave, for example, 3–10 Hz.

The detection approach applied to the filtered output supplied by the narrow band filter 41 may be the same as discussed for the QRS detection, e.g., automatic or manual gain control, dual comparator, etc. A dual comparator 44 having respective threshold inputs T3 and T4 is illustrated in FIG. 5, which accommodates the possibility that the T-wave may have either a positive or negative polarity. The output of the comparator 44 supplies one input 42 to an AND gate 45, which outputs to a delay stage 49. The delay stage 49 delays application of a shock to the patient for a programmable interval, e.g., zero to 100 milliseconds.

The second input 46 to the AND gate 45 is derived from the output 34 of the QRS detector. In the circuit of FIG. 5, the second input 46 to the AND gate 45 is derived by generating it a selected interval after the QRS complex is detected, e.g., a blanking interval of 50 milliseconds. In discrete logic, such an interval, or "window," can be implemented by a monostable multivibrator, while in software, it may be programmed.

Implementing a blanking interval prevents a shock from being falsely delivered during the QRS interval. Thus, only after the blanking interval is T-wave detection possible.

Figure 6:
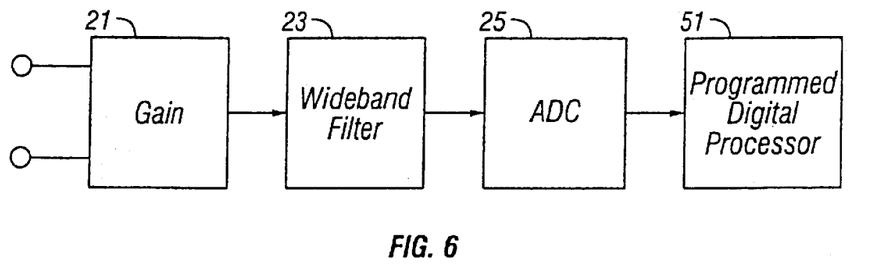
FIG. 6 is a block diagram depicting implementation of a wide band filter in analog hardware and remaining functions implemented digitally.

As one skilled in the art will appreciate, one can implement the functionality illustrated in FIGS. 1–5 with analog hardware, digital software, digital hardware, or various combinations thereof. One particularly useful hybrid configuration is illustrated in FIG. 6 where an analog gain stage 21 outputs to an analog wideband filter 21 which supplies a filtered output to an AID converter 25. The digital output of the A/D 25 is provided to a programmed digital processor 51, which is programmed to perform the functions of FIGS. 4 and 5 which follow analog to digital conversion in those Figures. Such circuitry could employ the analog to digital conversion approach of co-pending application of Alan H. Ostroff, Ser. No. 10/011,948, entitled Low Power A/D Converter filed on even date herewith and assigned to Cameron Health.

The programmable delay represented by delay stage 49 may also allow, for example, the doctor to manually delay delivering of the shock to the patient. The physician lot might want to add some number of milliseconds in addition to the point where the apparatus signals a T-wave detection in order to provide a primary adjustment on exactly where the shock hits the T-wave. To advance the automatic delivery of the shock in the circuit of FIG. 5, one may lower the threshold of the T-wave detection.

Another alternative is to employ a differentiator for purposes of T-wave detection. In such case, the circuitry takes the derivative of the T-wave and employs that derivative in a detection algorithm.

It can prove advantageous to implement the wide band filter 21 in analog hardware, since such an implementation is simple and straightforward. The remaining functions may then be implemented digitally, as shown, for example, in FIG. 6.

As those skilled in the art will appreciate, one can implement much more functionality with much less power in the digital domain than in the analog domain. The digital domain also lends itself better to modeling, prototype verification, and fine tuning.

The programmability of the delay element 49 further permits a "manual" mode of operation of the apparatus of FIGS. 4 and 5, wherein, rather than relying on automatic detection of the T-wave, the physician selects a fixed point in time after automatic detection of the QRS complex to apply the fibrillating shock. This fixed point may be selected to occur in the range of zero to 500 milliseconds after QRS detection. In such case, the comparator output 34 is switched into the delay stage 49 rather than the output of the AND gate 45. In this manner, the QRS detection triggers the shock after the period of delay provided by the delay stage 49 as set by the physician.

As another option, pacing of the patient according to FIG. 2 is applied to the patient, and the physician selects the delay supplied by delay element 49 to be equal to or greater than the coupling interval determined by pacing. This embodiment again uses the comparator output 34 as the input to trigger an output by the delay stage 49 at a selected point on or after expiration of the coupling interval.

In summary, in the above-disclosed systems, the timing or occurrence of the QRS complex is first ascertained and then the timing of the T-wave is detected. Prior to actual detection and shocking, a training or learning process or algorithm is performed on a selected number of intrinsic heartbeats to set parameters to be used in the detection process. Once the necessary information is acquired and stored, the system is set to detect the QRS complex. Once the QRS complex is detected, the system awaits the occurrence of the next T-wave, detects it, and delivers the shock.

As an option to the foregoing approach, a semi-automatic approach may be employed where the system detects the QRS complex, and the physician sets the timing for the shock, thus avoiding automatic detection of the T-wave. The physician may estimate T-wave occurrence from an ECG monitor other display of the cardiac waveform, which, of course, runs the risk implied by the intrinsic variability of the patient's cardiac waveform.

Once a shock has been delivered, the circuitry may then detect whether ventricular fibrillation (VF) occurred and, if it didn't, the T-wave detection may be re-initiated either automatically or manually. One can program a delay, i.e., how many seconds or heartbeats one wants to wait, and then how many shocks and T shocks until it's successful. In fact, one can also build in an automatic dithering capability wherein a state machine controlling the overall process automatically extends "it" and, if that doesn't work, the state machine automatically drops the T-wave detection threshold to cause earlier detection and, if that doesn't work, the state machine extends it even further and drops the threshold further. In other words, the circuit dithers about the point where the T-wave was expected to be.

While the present invention has been described above in terms of specific embodiments, it is to be understood that the invention is not limited to the disclosed embodiments. On the contrary, the following claims are intended to cover various modifications and equivalent methods and structures included within the spirit and scope of the invention.

What is claimed is:

1. A method of delivering a T-shock comprising the steps of:
    automatically detecting the occurrence of a QRS complex;
    automatically detecting the occurrence of a T-wave following said QRS complex; and
    responding to the automatic detection of said T-wave to deliver a shock.

2. The method of claim 1 wherein said step of automatically detecting the occurrence of the QRS complex employs a peak detection technique.

3. The method of claim 2 wherein said peak detection technique employs a manually set threshold.

4. The method of claim 3 wherein said peak detection technique employs a threshold set by an automatic gain control technique.

5. The method of claim 1 further including the step of employing a training algorithm to set expected parameters for the QRS complex and T-wave.

6. The method of claim 1 wherein the step of automatically detecting the occurrence of the T-wave employs narrow band filtering to select the T-wave component.

7. The method of claim 1 wherein the step of automatically detecting the QRS complex employs narrow band filtering to select the QRS component.

8. The method of claim 7 wherein the step of automatically detecting the occurrence of the T-wave employs a peak detection technique.

9. method of claim 8 wherein said peak detection technique employs a manually set threshold.

10. method of claim 8 wherein said peak detection technique employs a threshold set by an automatic gain control technique.

11. method of claim 1 wherein said shock is delivered automatically in response to detection of said T-wave.

12. method of claim 1 wherein said shock is delivered manually in response to detection of said T-wave.

13. An apparatus comprising:
    a programmed digital processor; and
    programmed process steps executable by said digital processor to detect occurrence of a QRS complex and to detect occurrence of a T-wave following said QRS complex;
    wherein said programmed process steps are further executable to implement narrowband filtering to select the T-wave.

14. The apparatus of claim 13 wherein said programmed process steps are further executable to implement narrowband filtering to select the QRS complex.

15. The apparatus of claim 13 wherein said programmed process steps are further executable to control delivery of a shock in response to detection of said T-wave.

16. The apparatus of claim 15 wherein said programmed process steps are further executable to detect a peak in said QRS complex.

17. The apparatus of claim 16 wherein programmed process steps are further executable to detect a peak in said T-wave.

18. The apparatus of claim 16 wherein said programmed process steps are further executable to implement automatic gain control in connection with detecting a peak in said QRS complex.

19. The apparatus of claim 16 wherein said programmed process steps are further executable to implement automatic gain control in connection with detecting a peak in said QRS complex in said T-wave.

20. The apparatus of claim 13 wherein said programmed process steps are further operable to implement an algorithm for determining an expected parameter of said QRS complex.

21. The apparatus of claim 13 wherein said programmed process steps are further operable to implement an algorithm for determining an expected parameter of said QRS complex in said T-wave.

22. An apparatus comprising:
  means for detecting a QRS complex in a cardiac waveform;
  means responsive to detection of the QRS complex for detecting a T-wave following said QRS complex; and
  means responsive to detection of the T-wave form to deliver a shock.

23. The apparatus of claim 22 wherein said means for detecting a QRS complex employs a peak detection technique.

24. The apparatus of claim 23 wherein said peak detection technique employs a manually set threshold.

25. The apparatus of claim 24 wherein said peak detection technique employs a threshold set by an automatic gain control technique.

26. The apparatus of claim 22 further including means for employing a training interval for deriving expected parameters for the QRS complex and T-wave.

27. The apparatus of claim 22 wherein said means for detecting the QRS complex employs narrow band filtering to select a QRS component.

28. The apparatus of claim 27 wherein said means for detecting the occurrence of the T-wave employs a peak detection technique.

29. The apparatus of claim 28 wherein said peak detection technique employs a manually set threshold.

30. The apparatus of claim 28 wherein said peak detection technique employs a threshold set by an automatic gain control technique.

31. The apparatus of claim 22 wherein said shock is delivered automatically in response to detection of said T-wave.

32. The method of claim 22 wherein said shock is delivered manually in response to detection of said T-wave.

33. An apparatus comprising:
  means for detecting a QRS complex in a cardiac waveform; and
  means responsive to detection of the QRS complex for detecting a T-wave following said QRS complex;
  wherein said means for detecting the T-wave employs narrow band filtering to select a T-wave component.

34. In a subcutaneous implantable cardioverter-defibrillator, the method comprising the steps of:
  automatically detecting the occurrence of a QRS complex; and
  responding to detection of the QRS complex by delivering a fibrillating shock to a patient;
  wherein said step of responding comprises the steps of:
    automatically detecting the occurrence of a T-wave following the QRS complex; and
    automatically delivering said shock in response to the automatic detection of the T-wave.

35. The method of claim 34 wherein said defibrillator applies a pacing waveform to a patient and wherein said step of responding comprises delivering said shock at a selected point in time on or after expiration of the coupling interval.

36. The method of claim 34 wherein said step of responding comprises automatically delivering said shock at a point in time separated from the point of automatic detection by a manually selected time interval.

* * * * *

UNITED STATES PATENT AND TRADEMARK OFFICE
CERTIFICATE OF CORRECTION

PATENT NO. : 6,834,204 B2
DATED : December 21, 2004
INVENTOR(S) : Alan H. Ostroff et al.

It is certified that error appears in the above-identified patent and that said Letters Patent is hereby corrected as shown below:

Title page,
Item [54], Title, delete "DEFIBRILLATION", and insert therefor
-- FIBRILLATION --.

Column 6,
Line 44, delete "AID", and insert therefor -- A/D --.
Line 55, delete "lot".

Column 8,
Lines 30, 32, 35 and 37, before "method", insert -- The --.

Column 10,
Line 7, delete "method", and insert therefor -- apparatus --.

Signed and Sealed this

Tenth Day of May, 2005

JON W. DUDAS
*Director of the United States Patent and Trademark Office*